(12) United States Patent
Notohara et al.

(10) Patent No.: US 8,948,339 B2
(45) Date of Patent: Feb. 3, 2015

(54) RADIATION TOMOGRAPHY APPARATUS

(75) Inventors: Daisuke Notohara, Kyoto (JP);
Kazuyoshi Nishino, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 371 days.

(21) Appl. No.: 13/522,192

(22) PCT Filed: Jan. 15, 2010

(86) PCT No.: PCT/JP2010/000208
§ 371 (c)(1),
(2), (4) Date: Jul. 13, 2012

(87) PCT Pub. No.: WO2011/086604
PCT Pub. Date: Jul. 21, 2011

(65) Prior Publication Data
US 2013/0216020 A1 Aug. 22, 2013

(51) Int. Cl.
*A61B 6/03* (2006.01)
*A61B 6/02* (2006.01)
*A61B 6/06* (2006.01)
(52) U.S. Cl.
CPC .... *A61B 6/02* (2013.01); *A61B 6/06* (2013.01)
USPC ................... 378/21; 378/22; 378/23; 378/24; 378/25; 378/26; 378/27
(58) Field of Classification Search
CPC .................. G06T 11/005; G06T 2207/10116; G06T 2207/10081; Y10S 378/901
USPC ..................................... 378/21–27
See application file for complete search history.

(56) References Cited

U.S. PATENT DOCUMENTS 6,643,351 B2 11/2003 Morita et al.
6,973,157 B2 * 12/2005 Claus ................................. 378/8
7,925,074 B2 * 4/2011 Patnaik .......................... 382/149

FOREIGN PATENT DOCUMENTS

JP        2002-26309 A      9/2002

* cited by examiner

*Primary Examiner* — Michael Maskell
(74) *Attorney, Agent, or Firm* — McDermott Will & Emery LLP

(57) ABSTRACT

One object of this invention is to provide a radiation tomography apparatus for acquiring a tomographic image from a plurality of fluoroscopic images. The radiation tomography apparatus can acquire the tomographic image having superior visibility without being influenced by a shadow of a collimator appearing in the fluoroscopic image when radiation is applied only to a portion of an FPD through control of the collimator. In this invention, a boundary between a shadow area where the shadow of the collimator appears in the fluoroscopic image and a non-shadow area is identified, and the shadow area in the fluoroscopic image is complemented by the non-shadow area, etc., whereby a complement image is generated. Then the complement image is used for generating the tomographic image. According to this invention, an extremely dark area where the shadow of the collimator appears is removed and thereafter the tomographic image is generated. As a result, the tomographic image has superior visibility with no blurring due to the shadow of the collimator.

8 Claims, 8 Drawing Sheets

RADIATION TOMOGRAPHY APPARATUS

RELATED APPLICATIONS

This application is the U.S. National Phase under 35 U.S.C. §371 of International Application No. PCT/JP2010/000208, filed on Jan. 15, 2010, the disclosure of which Application is incorporated by reference herein.

TECHNICAL FIELD

This invention relates to a radiation tomography apparatus provided with a radiation source and an FPD. In particular, this invention relates to a radiation tomography apparatus in which a series of fluoroscopic images are taken while the radiation source and the FPD move synchronously in opposite directions to each other to obtain a tomographic image of a subject based on the fluoroscopic images.

BACKGROUND ART

Medical institutions are equipped with a radiographic apparatus 51 for obtaining a tomographic image of a subject M. Such radiographic apparatus 51 includes a configuration in which a radiation source 53 that emits radiation and an FPD 54 that detects radiation move synchronously to continuously take a series of fluoroscopic images, and then the series of fluoroscopic images are superimposed to obtain the tomographic image (see FIG. 16.) In such radiographic apparatus 51, during taking a series of fluoroscopic images, the radiation source 53 and the FPD 54 move along a body axis direction of the subject as to approach to each other, thereby having the same position in the body axis direction. Thereafter, the radiation source 53 and the FPD 54 move along the body axis direction as to be spaced away from each other. Such radiographic apparatus is described, for example, in Cited Document 1. See Patent Literature 1.

The radiation source 53 has a collimator 53a attached thereto. Control of the collimator 53a can achieve limitation of a range where the radiation source 53 emits radiation. When the collimator 53a is controlled such that radiation is emitted to only a site of interest of the subject, unnecessary exposure to the subject can be suppressed. See FIG. 17.

Description will be given of the foregoing operation of taking the tomographic image by the radiographic apparatus 51. Firstly, the radiation source 53 intermittently emits radiation while moving. Specifically, the radiation source 53 moves along the body axis direction of the subject for every completion of irradiation, and again emits radiation. In this way, 74 fluoroscopic images are obtained, and then superimposed. The finished image is a tomographic image having a sectional image appearing therein when the subject is cut along a sectional plane.

[Patent Literature 1] Japanese Patent Publication No. 2002-263093

The conventional configuration as above, however, has the following problem. That is, in the radiographic apparatus 51 with the conventional configuration, a shadow of the collimator 53a appearing in the fluoroscopic image may affect acquisition of a tomographic image. Moreover, as the collimator 53a is controlled such that a radiation beam B emitted toward an FPD 54 is narrower, a range of incident radiation in the FPD 54 becomes smaller, accordingly. As a result, no radiation enters in the periphery of the FPD 54, as shown in FIG. 17.

The acquired 74 fluoroscopic images are images relating to the entire FPD 54. Consequently, the periphery of the FPD 54 where no radiation is detected is to be displayed in the periphery of the fluoroscopic image with the narrower radiation beam B. That is because the fluoroscopic images contain the entire FPD 54. Then a frame-shape dark area appears in the periphery of the fluoroscopic image acquired with the narrower radiation beam B. This dark area is a shadow of the collimator 53a falling on the fluoroscopic image.

When a tomographic image is acquired through superimposing the fluoroscopic images with the frame-shape dark areas remaining therein, the shadows of the collimator 53a are superimposed on the sectional image. The radiographic apparatus 51 takes a plurality of fluoroscopic images in various radiography directions, and generates a tomographic image based on profile views of the subject falling on the fluoroscopic images in various shapes. The shadow of the collimator 53a appears independently of the subject. Consequently, when the tomographic image is acquired through superimposing the fluoroscopic images, an image of the subject is to be reconstructed while the shadows independent of the subject are superimposed.

Then, the sectional image is blurred due to influences by the shadows of the collimator 53a. The image is extremely blurred in a boundary between the shadow of the collimator 53a and the image of the subject. More particularly, as shown in FIG. 18, the image is blurred notably at both ends of the tomographic image D in a direction where the FPD 54 and the radiation source 53 move (i.e., a vertical direction of the tomographic image D.)

This invention has been made regarding the state of the art noted above, and its object is to provide a radiation tomography apparatus for acquiring a tomographic image from a plurality of fluoroscopic images. The radiation tomography apparatus can acquire the tomographic image having superior visibility without being influenced by shadows of a collimator falling on the fluoroscopic images when radiation is applied only to a portion of an FPD through control of the collimator.

SUMMARY

This invention is constituted as stated below to achieve the above object. One example of the invention is a radiation tomography apparatus including a radiation source for irradiating a subject with radiation; a collimator for collimating radiation from the radiation source; a radiation detecting device for detecting radiation applied to the subject; a top board between the radiation source and the radiation detecting device for supporting the subject placed thereon; a moving device for moving the radiation source and the radiation detecting device synchronously in opposite directions to each other along the top board; a movement controlling device for controlling the moving device; an image generating device for generating a fluoroscopic image in accordance with detection signals outputted from the radiation detecting device; a boundary identifying device for identifying from the fluoroscopic image a boundary between a shadow area and a non-shadow area in the fluoroscopic image, in the shadow area a shadow of the collimator appearing and in the non-shadow a shadow of the collimator not appearing; an image complement device for generating a complement image through complementing the shadow area in the fluoroscopic image with a complement value with reference to the boundary, the complement value indicating a pixel value of the non-shadow area or indicating a pixel value nearer to that of the non-shadow area than that of the shadow area; and a superimposing device for superimposing a series of the complement images generated from a series of the fluoroscopic images that are continuously taken while the radiation source and the radiation detecting device move to generate a tomographic image.

[Operation and Effect]

The radiation tomography apparatus according to the example of the invention includes the collimator for collimating radiation emitted from the radiation source. The fluoroscopic image contains the shadow area where the shadow of the collimator falls. According to the example of the invention, the boundary between the shadow area and the non-shadow area in the fluoroscopic image is identified, and the shadow area is complemented by the complementation value indicating the pixel value of the non-shadow area or the pixel value nearer to that of the non-shadow area than that of the shadow area, whereby a complement image is generated. Then the tomographic image is generated with the complement image. Since the collimator is provided for restricting the range of radiation irradiation, no radiation transmits through the collimator. Consequently, the shadow area of the fluoroscopic image is extremely dark compared to the non-shadow area, and thus is obstructive to generation of the tomographic image. According to the example of the invention, the extremely dark area is removed and thereafter the tomographic image is generated. As a result, the tomographic image has superior visibility with no blurring due to the shadow of the collimator.

Moreover, in the foregoing radiation tomography apparatus, the boundary identifying device preferably identifies the boundary in a direction orthogonal to the moving direction on ends of the fluoroscopic image in the moving direction. The image complement device preferably generates the complement image through obtaining a strip region in the non-shadow area of the fluoroscopic image that laterally extends in the orthogonal direction and arranging the strip regions in the shadow area of the fluoroscopic image in the moving direction.

[Operation and Effect]

The foregoing configuration is a concrete example of generating the complement image. That is, the boundary identifying device identifies the boundary extending along a vertical direction in the fluoroscopic image and appearing on ends of the fluoroscopic image in the moving direction. The image complement device obtains a strip region in the non-shadow area of the fluoroscopic image that laterally extends in the orthogonal direction, and arranges the strip regions in the shadow area, thereby generating the complement image. Such configuration can achieve enhanced visibility at the ends of the tomographic image in the moving direction having extreme blurring.

Moreover, in the foregoing radiation tomography apparatus, the boundary identifying device preferably identifies the boundary through operating an image filter successively while moving it in the moving direction in the fluoroscopic images. The image filter acts on a partial range of an identification region that extends longitudinally along the moving direction in the fluoroscopic image.

[Operation and Effect]

The foregoing configuration is a concrete example of identifying the boundary between the shadow area and the non-shadow area in the fluoroscopic image. Specifically, the boundary is identified for a portion of the fluoroscopic image (i.e., an identification region), and thus rapid operation can be achieved. The image filter repeatedly acts on a portion of the identification region, whereby image processing is performed to the entire region. Such configuration can achieve boundary identification with ease by a simple image-processing method.

Moreover, in the foregoing radiation tomography apparatus, the boundary identifying device preferably operates the image filter successively from a first end toward a center of the identification region in the moving direction.

[Operation and Effect]

The foregoing configuration is a concrete example of operating the image filter. Specifically, the image filter is operated successively from a first end toward a center of the identification region in the moving direction. Here the shadow of the collimator appears at the periphery of the fluoroscopic image. Thus, when the image filter acts on the fluoroscopic image from the end thereof, the boundary can be identified more rapidly.

Moreover, in the foregoing radiation tomography apparatus, the boundary identifying device preferably identifies the boundary on the first end in the moving direction in the identification region and thereafter identifies the boundary on a second end in the moving direction in the identification region through operating the image filter successively from the second end toward the center of the identification region. The image complement device preferably complements each two shadow areas in the fluoroscopic image with reference to the positions of the two identified boundaries.

[Operation and Effect]

The foregoing configuration is a further concrete example of operating the image filter. Specifically, the image filer is operated to identify the boundary on the first end in the identification region and thereafter operated from the second end in the identification region to identify another boundary. Since the shadow of the collimator generally appears in both ends of the fluoroscopic image, such configuration can achieve immediate identification of the two boundaries.

Moreover, in the foregoing radiographic apparatus, the image filter used by the boundary identifying device is preferably a differentiation filer with a matrix of m rows and n columns.

[Operation and Effect]

The foregoing configuration is a concrete example of the image filter. When the differentiation filter is adopted as the image filter, sharp variations in the pixel values on the boundary between the shadow area and the non-shadow area are not missed, and thus the boundary can be identified with high accuracy.

Moreover, in the foregoing radiographic apparatus, the differentiation filter preferably has the rows arranged in the moving direction in the fluoroscopic image. The image complement device preferably obtains the strip region from a position that is spaced away from the boundary by an m-pixel in the non-shadow area of the fluoroscopic image.

[Operation and Effect]

The foregoing configuration is a concrete example of obtaining the strip region used for complementation of the shadow area. It is difficult to distinguish exactly the boundary between the shadow area and the non-shadow area even with the differentiation filter. According to this example of the invention, the strip region is obtained from a position spaced somewhat away from the boundary in the non-shadow area for ensuring location of the strip region in the non-shadow area. Here, it is sufficient that the strip region is spaced away from the boundary by a distance of the number of rows of the differentiation filter.

Moreover, in the foregoing radiographic apparatus, the boundary identifying device preferably averages the identification regions having an orthogonal width in an orthogonal direction and generates a profile with the orthogonal pixel width corresponding to one pixel. The image filter preferably acts on this profile.

[Operation and Effect]

The foregoing configuration represents more rapid operation in identification of the boundary. The identification region is profiled once and then the image filter acts on this, whereby a processing using the image filter can be achieved at a higher speed.

DESCRIPTION OF REFERENCES b . . . boundary
C . . . complement image
cp . . . profile
D . . . tomographic image
F . . . differentiation filter (image filter)
J . . . identification region
P . . . fluoroscopic X-ray image (fluoroscopic imaging)
R1 . . . shadow area
R2 . . . non-shadow area
t . . . strip region
3 . . . X-ray tube (radiation source)
3a . . . collimator
4 . . . FPD (radiation detecting device)
7 . . . synchronously moving mechanism (moving device)
8 . . . synchronous movement control section (movement control device)
11 . . . image generating section (image generating device)
12 . . . boundary identifying section (boundary identifying device)
13 . . . image complement section (image complement device)
14 . . . superimposing section (superimposing device)

DETAILED DESCRIPTION

Each example of radiation tomography apparatus according to this invention will be described hereinafter with reference to the drawings. Herein, X-rays in each example correspond to radiation in this invention.

Example 1

Figure 1:
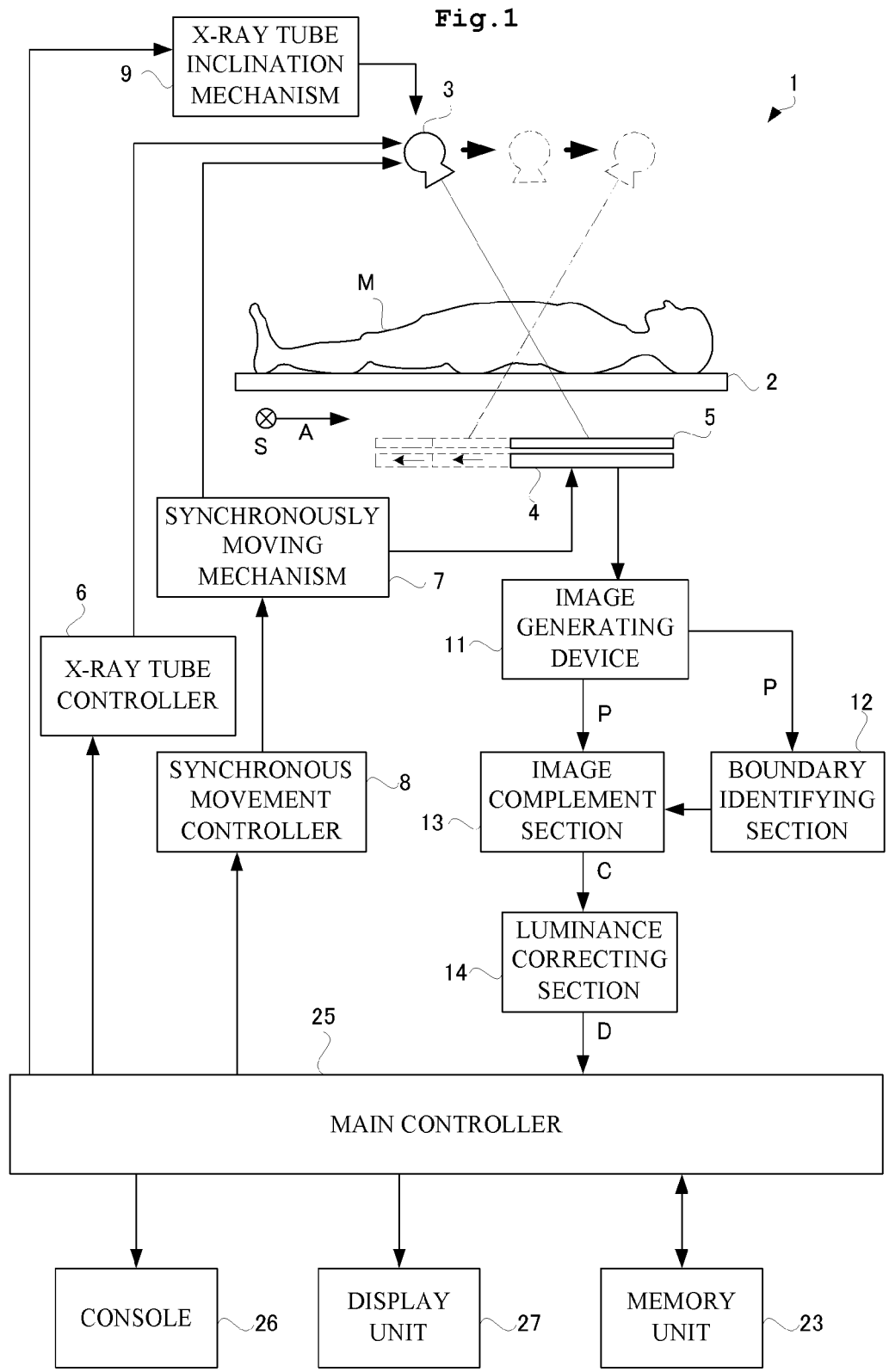
FIG. 1 is a functional block diagram showing an X-ray apparatus according to one example of the invention.

FIG. 1 is a functional block diagram showing a configuration of radiation tomography apparatus according to Example 1. As shown in FIG. 1, an X-ray apparatus 1 in Example 1 includes a top board 2 for supporting a subject M placed thereon as a target for X-ray tomography, an X-ray tube 3 disposed above the top board 2 (on a first surface side of the top board 2) for irradiating the subject M with an X-ray beam in a cone shape, a flat panel X-ray detector (hereinafter, abbreviated as FPD) 4 disposed below the top board 2 (on a second surface side of the top board 2) for detecting an image of the subject M through which X-rays transmit, a synchronously moving mechanism 7 and a synchronous movement controller 8 for controlling thereof, the synchronously moving mechanism 7 moving the X-ray tube 3 and the FPD 4 synchronously in opposite directions to each other across a site of interest of the subject M while a center axis of the X-ray beam in a cone shape always conforms to a center of the FPD 4, an X-ray grid 5 provided as to cover an X-ray detecting surface of the FPD 4 detecting X-rays of the FPD 4 for absorbing scattered X-rays. In this way, the top board 2 is placed between the X-ray tube 3 and the FPD 4. The X-ray tube 3 corresponds to the radiation source in this invention. The FPD 4 corresponds to the radiation-detecting device in this invention. The synchronous movement controller 8 corresponds to the movement control device in this invention. The synchronously moving mechanism 7 corresponds to the moving device in this invention.

The X-ray tube 3 is constructed to repeat irradiation of the subject M with the cone-shaped and pulsed X-ray beam under control by the X-ray tube controller 6. The X-ray tube 3 has a collimator 3a attached thereto for collimating the X-ray beam into a shape of a pyramid cone. The X-ray tube 3 and the FPD 4 constitute imaging systems 3 and 4 for taking X-ray fluoroscopic images.

The X-ray apparatus 1 according to Example 1 further includes a main controller 25 for performing overall control of the controllers 6 and 8, and a display unit 27 for displaying a tomographic image. The main controller 27 has a CPU, and provides each controller 6, 8, 22 and each section 11, 12, 13, 14, to be mentioned later, by executing various programs.

The synchronously moving mechanism 7 moves the X-ray tube 3 and the FPD 4 synchronously. The synchronously moving mechanism 7, under control of the synchronous movement controller 8, moves the X-ray tube 3 straight along a linear track parallel to the direction of the body axis A of the subject M (a longitudinal direction of the top board 2.) The X-ray tube 3 and the FPD 4 each have a moving direction corresponding to the longitudinal direction of the top board 2. Moreover, the cone-shaped X-ray beam emitted from the X-ray tube 3 during examination is always emitted toward the site of interest of the subject M. The X-ray emission angle is changed, for example, from an initial angle of −20° to a final angle of 20° by changing an angle of the X-ray tube 3. An X-ray tube inclination mechanism 9 performs such changes of the X-ray emission angle.

The synchronously moving mechanism 7 moves the FPD 4, disposed below the top board 2, straight along the direction of the body axis A of the subject M (the longitudinal direction of the top board 2), synchronously with straight movement of the X-ray tube 3 noted above. The moving direction thereof is opposite to the moving direction of the X-ray tube 3. That is, the cone-shaped X-ray beam with the emission source position and the direction of emission changing through movement of the X-ray tube 3 is always received on the entire X-ray detecting plane of the FPD 4. Thus, for one examination, the FPD 4 acquires 74 fluoroscopic X-ray images P, for example, while synchronously moving together with the X-ray tube 3 in opposite directions. Specifically, the imaging systems 3 and 4 move, as opposed to each other, from an initial position shown by solid lines through a position shown by dashed lines toward a position shown by alternate long and short dash lines. That is, a plurality of X-ray fluoroscopic images are acquired while changing positions of the X-ray tube 3 and the FPD 4. Since the cone-shaped X-ray beam is always received on the entire X-ray detecting surface of the FPD 4, the center axis of the cone-shaped X-ray beam always conforms to the center of the FPD 4 during radiography. During radiography, the center of the FPD 4 moves straight, and this movement is opposite to the direction of movement of the X-ray tube 3. In other words, the X-ray tube 3 and the FPD 4 move synchronously and adversely to each other along the body axis direction A.

Description will be given of the collimator 3*a* provided in the X-ray apparatus 1. The collimator 3*a* is attached to the X-ray tube 3 for collimating X-rays emitted from the X-ray tube 3 to generate an X-ray beam B in a quadrangular pyramid (cone) shape.

Figure 2:
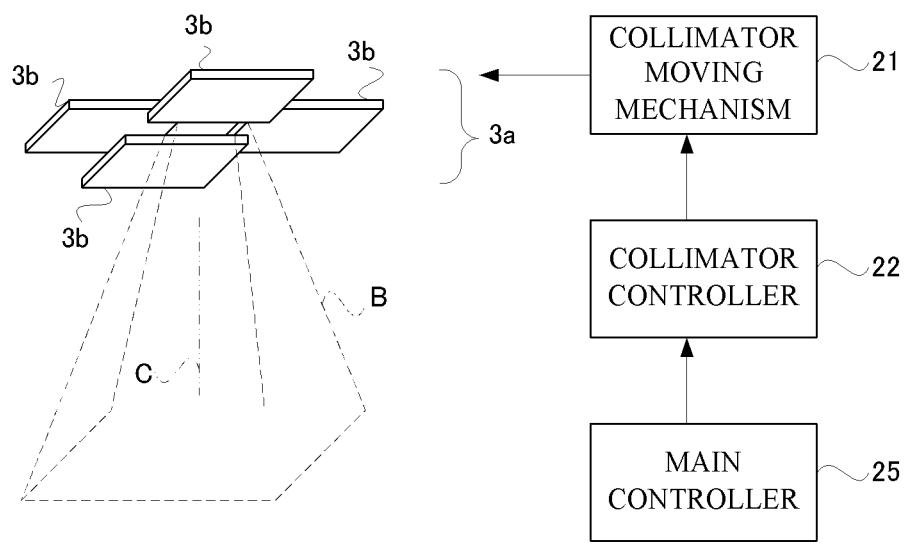
FIG. 2 is a perspective view showing a collimator according to the example of the invention.

The collimator 3*a* is to be described in detail. As shown in FIG. 2, the collimator 3*a* has one pair of leaves 3*b* that moves in a mirror-image symmetrical manner relative to the center axis C, and has one more pair of leaves 3*b* that similarly moves in a mirror-image symmetrical manner relative to the center axis C. Movement of the leaves 3*b* of the collimator 3*a* can achieve not only irradiation of an entire detecting surface of the FPD 4 with an X-ray beam B in a cone shape, but also irradiation of only a center portion of the FPD 4 with an X-ray beam B in a fan shape. Here, the center axis C also represents the center of the X-ray beam B. One pair of the leaves 3*b* controls divergence of the quadrangular pyramid X-ray beam in the body axis direction of the subject. The other pair of the leaves 3*b* controls divergence of the X-ray beam in a body side direction of the subject. A collimator moving mechanism 21 changes opening of the collimator 3*a*. A collimator controller 22 controls the collimator moving mechanism 21.

Figure 3:
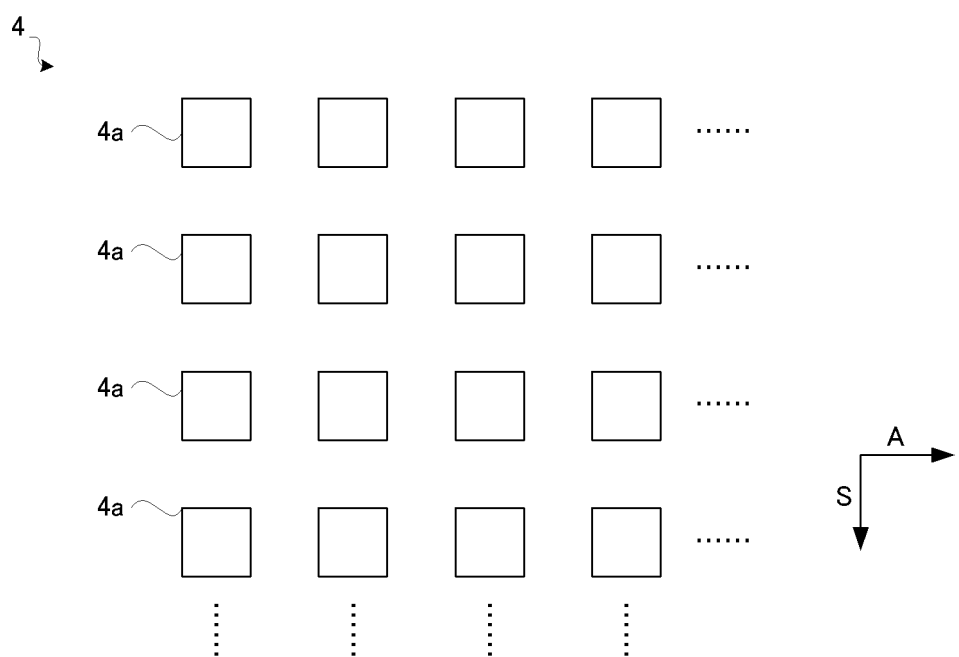
FIG. 3 is a schematic view showing an FPD according to the example of the invention.

Description will be given of a configuration of the FPD 4. As shown in FIG. 3, the FPD 4 has a detecting surface for detecting X-rays. X-ray detecting elements for detecting X-rays are arranged longitudinally and transversely on the detecting surface. For instance, 1024 X-ray detecting elements 4*a* are arranged in the body axis direction A of the subject M and 1024 X-ray detecting elements 4*a* are arranged in the body side direction S of the subject M. The arrangement pitch of X-ray detecting elements 4*a* is 300 μm both in the body axis direction A and the body side direction S. The fluoroscopic X-ray image P outputted from an image generating device 11, to be mentioned later, is generated in accordance with detection signals outputted from each X-ray detecting element 4*a*. Similar to the X-ray detecting element 4*a*, pixels are two-dimensionally arranged.

An image generating section 11 is provided downstream of the FPD 4 for generating a fluoroscopic X-ray image P in accordance with detection signals outputted from the FPD 4. See FIG. 1. Further downstream of the image generating section 11 is a boundary identifying section 12 for conducting given image analysis using the fluoroscopic X-ray image, an image complement section 13 for complementing the fluoroscopic X-ray image P, and a superimposing section 14 for superimposing the images to generate a tomographic image D. The superimposing section 14 corresponds to the superimposing device in the example of the invention. The boundary identifying section 12 corresponds to the boundary identifying device in the example of the invention. The image complement section 13 corresponds to the image complement device in the example of the invention. The image generating section 11 corresponds to the image generating device in the example of the invention.

Figure 4:
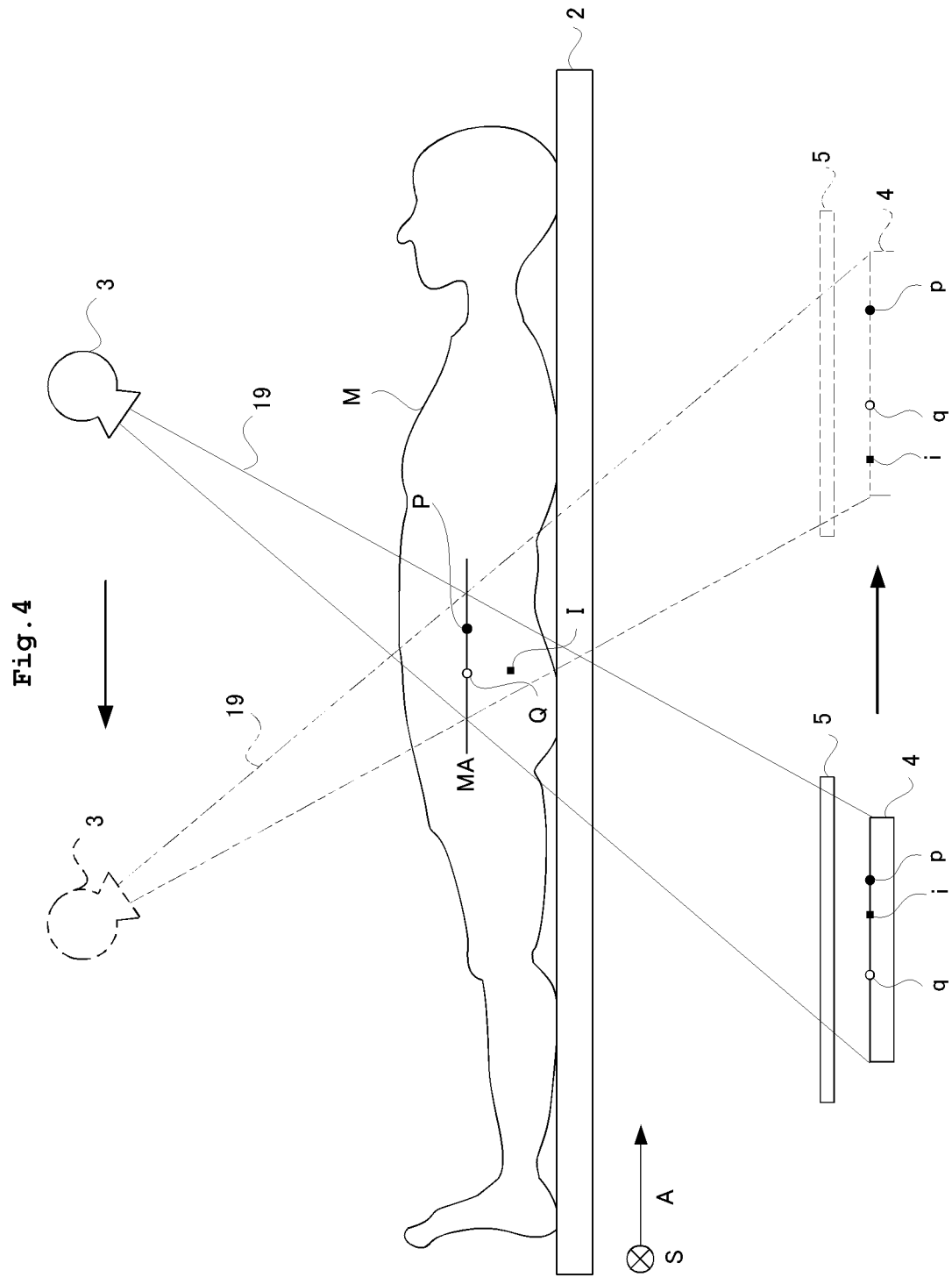
FIG. 4 is a schematic view showing a principle of tomography according to the example of the invention.

Next, description will be given of the principle of obtaining a tomographic image with the tomography X-ray apparatus 1 according to Example 1. FIG. 4 shows a method of obtaining a tomographic image with the X-ray apparatus according to Example 1. For instance, a reference sectional plane MA parallel to the top board 2 (horizontal relative to the vertical direction) as shown in FIG. 4 is to be described. The fluoroscopic image generation section 11 generates a series of fluoroscopic X-ray images P while the FPD 4 moves synchronously with and in an opposite direction to the X-ray tube 3 according to the direction where the X-ray tube 3 emits the cone-shaped X-ray beam B such that points P and Q located in the reference sectional plane MA are always projected on the fixed points p and q, respectively, on the X-ray detecting surface of the FPD 4. The projected image of the subject M appears in a series of the fluoroscopic X-ray images P while varying in position. Then, the superimposing section 14 superimposes the series of the fluoroscopic X-ray images P (to be precise, a complement image C having undergone a complement process to be mentioned later), thereby accumulating images located in the reference sectional plane MA (e.g. the fixed points p and q) to image it as an X-ray sectional image. On the other hand, a point I not located in the reference sectional plane MA appears in the series of the subject images as a point i, while varying in projected position in the FPD 4. As distinct from the fixed points p and q, such points i cause blurring, instead of forming an image, upon superimposing the X-ray fluoroscopic images by the superimposing section 14. The series of the fluoroscopic X-ray images P (the complement image C) are superimposed in this way, whereby an X-ray sectional image containing only the images located in the reference sectional plane MA of the subject M can be obtained. Thus, when the X-ray fluoroscopic images are simply superimposed, an X-ray sectional image on the reference sectional plane MA can be obtained. Here, a position of the reference sectional plane MA in the vertical direction corresponds to the reference sectional position in this invention.

Further, a similar sectional image can be obtained from any selected section parallel to the reference sectional plane MA, by changing settings of the superimposing section 14. Although the projected position of the point i described above moves on the FPD 4 during imaging, a speed of this movement increases as a distance increases between the point I prior to projection and the reference sectional plane MA. The series of subject images obtained in this way is superimposed while being shifted in the body axis direction A at given pitches, whereby an X-ray sectional image at a cutting position parallel to the reference sectional plane MA can be obtained. The superimposing section 14 superimposes the series of the subject images in this way. The method of obtaining a tomographic image in this way is referred to as a filter back projection.

Figure 5:
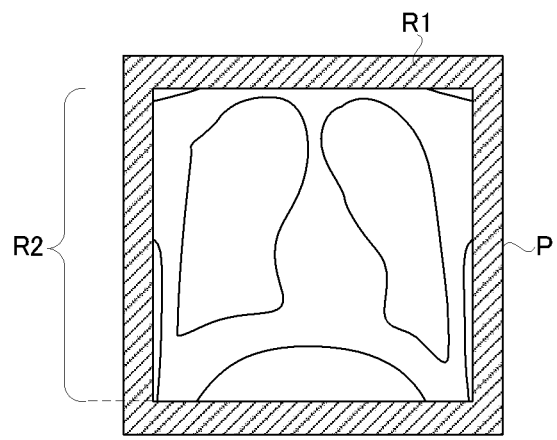
FIG. 5 is a schematic view of a fluoroscopic X-ray image according to the example of the invention.

Now, description will be given of a method for generating an X-ray fluoroscopic image by the image generating section 11. As shown in FIG. 5, a dark area in a frame shape appears in the fluoroscopic X-ray image P so as to rim the fluoroscopic X-ray image P. The image of the subject M appears inside of the dark area. The dark area corresponds to a shadow area R1 where a shadow of the leaves 3*b* of the collimator 3*a* appears and an image of the subject M does not appear. On the other hand, a rectangular area inside of the shadow area R1 corresponds to a non-shadow area R2 where the shadow of the leaves 3*b* does not appear and the image of the subject M appears. Since the leaves 3*b* transmit no X-ray, the shadow area R1 has a pixel value extremely smaller than the shadow area R2.

In comparison of the fluoroscopic X-ray image P taken while the imaging systems 3 and 4, the image of the subject M appearing in the fluoroscopic X-ray image P is shifted in a longitudinal direction in FIG. 5 (i.e., a direction corresponding to the moving directions of the imaging systems 3 and 4.) This occurs from variation in shape of the shadow of the subject M projected on the FPD 4 in accordance with shifting of the imaging systems 3 and 4 in the moving direction thereof. On the other hand, the shadow of the leaves 3b appearing in a series of the fluoroscopic X-ray images P is not sifted as the image of the subject M is shifted, but similarly appears in every fluoroscopic X-ray image.

If the fluoroscopic X-ray image P is used as it is for obtaining the tomographic image D, the shadow of the leaves 3b, independent of an internal structure of the subject M, is also superimposed unnecessarily to generate the tomographic image D. As a result, the tomographic image D of the subject M is blurred especially on both ends thereof in the longitudinal direction (i.e., a direction corresponding to the moving directions of the imaging systems 3 and 4.)

Figure 6:
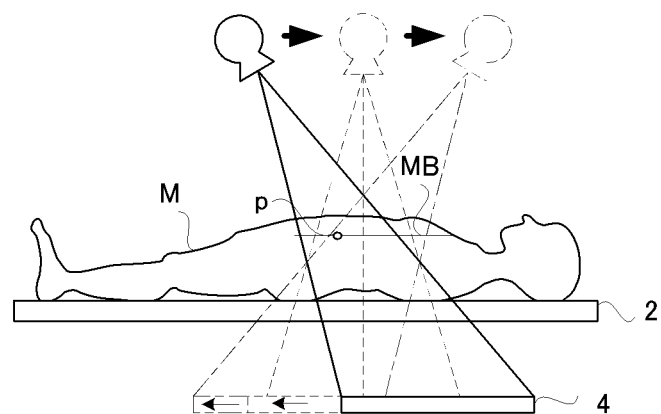
FIGS. 6 through 8 are schematic views each showing a principle of a blurred tomographic image due to a shadow of the collimator according to the example of the invention.

Description will be given of the principle of blurring in the tomographic image. It is assumed that a tomographic image of the subject M is generated for a cut surface MB including a point p inside the subject M shown in FIG. 6. It is apparent from FIG. 6 that a position where the point p appears on the FPD 4 is shifted gradually toward the end of the FPD 4 as the imaging systems 3 and 4 move. Specifically, when the imaging systems 3 and 4 are located in a position indicated by solid lines, the point p is located in the center of the X-ray beam. On the other hand, when the imaging systems 3 and 4 are shifted to a position indicated by alternate long and short dash lines, the point p is located at the end of the X-ray beam.

Figure 7:
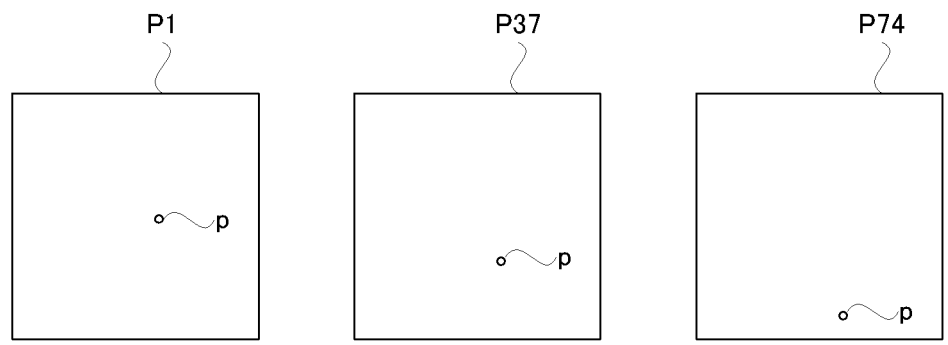

FIG. 7 schematically shows appearance of the point p in the 74 fluoroscopic X-ray images P. The fluoroscopic X-ray image P1 in the drawing represents an image taken for the first time and obtained when the imaging systems 3 and 4 are in the position indicated by solid lines in FIG. 6. The fluoroscopic X-ray image P37 in the drawing represents an image taken for the thirty-seventh time and obtained when the imaging systems 3 and 4 are in the position indicated by alternate long and short dash lines in FIG. 6. Moreover, the fluoroscopic X-ray image P74 in the drawing represents an image taken for the seventy-fourth time and obtained when the imaging systems 3 and 4 are in the position indicated by alternate long and short dash lines in FIG. 6. As is apparent from comparison of each fluoroscopic X-ray image P in order of obtaining the images, the point p is shifted toward the lower end of the fluoroscopic X-ray image P. The point p appears in every fluoroscopic X-ray image P while being shifted.

Figure 8:
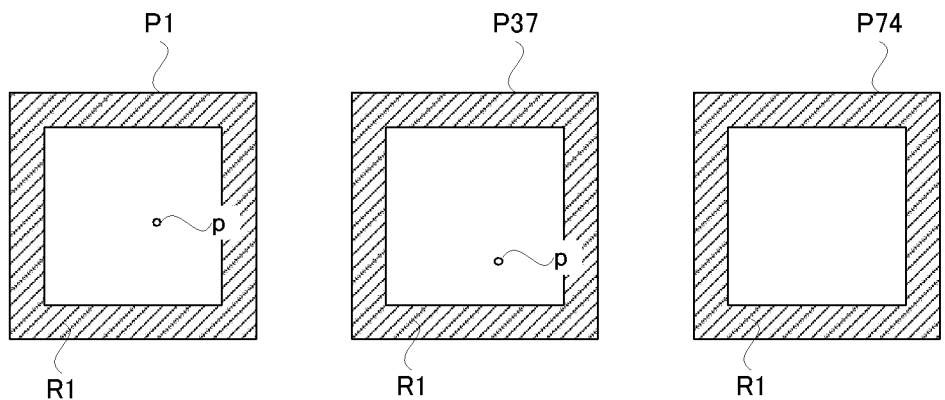

In the configuration of Example 1 with the collimator 3a, the shadow area R1 actually appears in every fluoroscopic X-ray image P as in FIG. 8. As shown in FIG. 8, the shadow of the leaves 3b of the collimator 3a appears in every fluoroscopic X-ray image P. Consequently, the image of the subject M that is to appear in the periphery of each fluoroscopic X-ray image P is hidden by the shadow area R1. The point p is shifted to the lower end of the fluoroscopic X-ray image P as the image P is successively taken, and finally is hidden by the shadow area R1. Thus, the point p does not appear in all the fluoroscopic X-ray images P.

When the point p is imaged on the tomographic image D using fluoroscopic X-ray image P as in FIG. 8, the shadow area R1 of extremely low luminance is also superimposed together. As a result, the point p has an extremely small pixel value. Such blurring in the tomographic image D is especially remarkable in the upper and lower ends thereof in the longitudinal direction as a direction corresponding to the moving directions of the imaging systems 3 and 4 in the tomographic image D.

Figure 9:
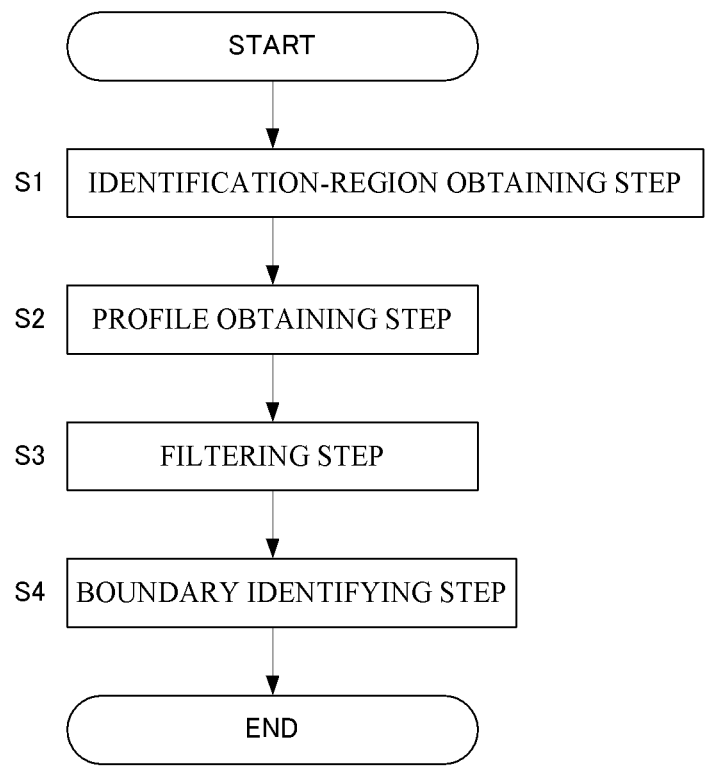
FIG. 9 is a flow chart showing operations of a boundary identifying section according to the example of the invention.

The boundary identifying section 12 and the image complement section 13 in Example 1 are provided in order to reduce blurring of the image in the tomographic image D. Firstly, description will be given of operations of the boundary identifying section 12. As shown in FIG. 9, the boundary identifying section 12 obtains an identification region J from the fluoroscopic X-ray image P (an identification-region obtaining step S1), and obtains a profile cp from the identification region J (a profile obtaining step S2.) Thereafter, the boundary identifying section 12 performs filtering to the profile cp (a filtering step S3), and identifies a boundary b between the shadow area R1 and the non-shadow area R2, described with FIG. 5, from the results (a boundary identifying step S4.) Each of these steps will be described in order.

Identification-Region Obtaining Step S1

Figure 10:
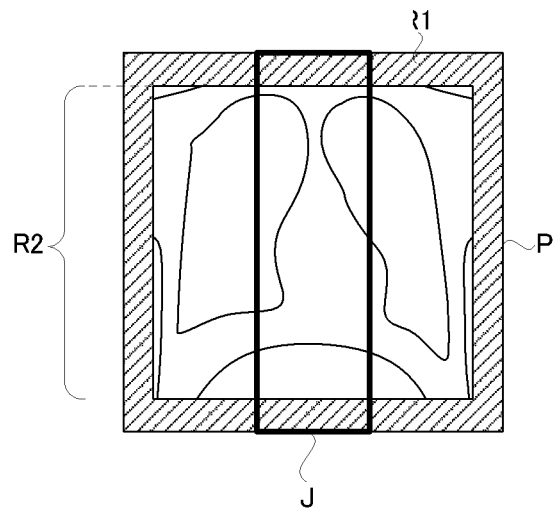
FIGS. 10 through 13 are schematic views each showing operations of the boundary identifying section according to the example of the invention.

Firstly, the boundary identifying section 12 obtains a fluoroscopic X-ray image P from the image generating section 11, and sets a region used for identifying the boundary b. FIG. 10 shows the identification region J set by the boundary identifying section 12. The identification region J extends longitudinally along the longitudinal direction of the fluoroscopic X-ray image P (the moving direction), and includes both ends of the fluoroscopic X-ray image P in the longitudinal direction. Moreover, the identification region J has a width by 64 to 128 pixels, for example, in a transverse direction of the fluoroscopic X-ray image P (i.e., a direction orthogonal to the moving directions of the imaging systems 3 and 4), and is located at the center of the fluoroscopic X-ray image P in the transverse direction.

Profile Obtaining Step S2

Figure 11:
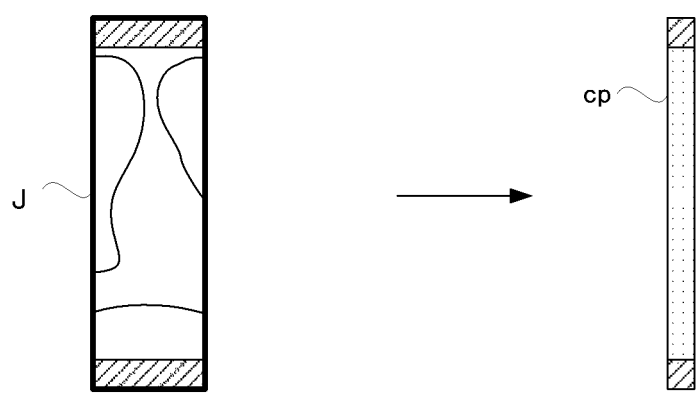

Next, the boundary identifying section 12 obtains the profile cp based on the identification region J. FIG. 11 shows operation of the boundary identifying section 12 at that time. The boundary identifying section 12 calculates an average value through averaging the pixel values of the pixels arranged in the transverse direction of the identification region J (the orthogonal direction). The boundary identifying section 12 calculates such average value successively in the longitudinal direction of the identification region J (the moving direction), thereby generating the profile cp having the average values arranged in the longitudinal direction. The profile cp is one-dimensional data having the average values arranged in one column.

Filtering Step S3

Figure 12:
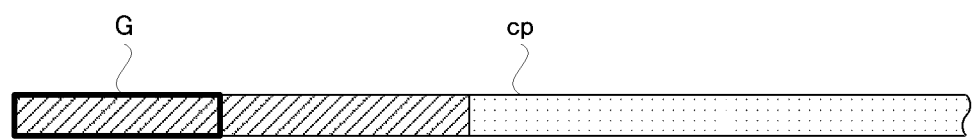
Figure 12:
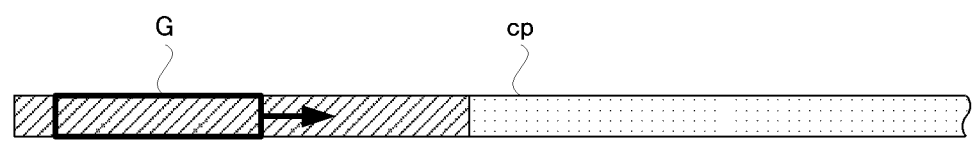
Figure 12:
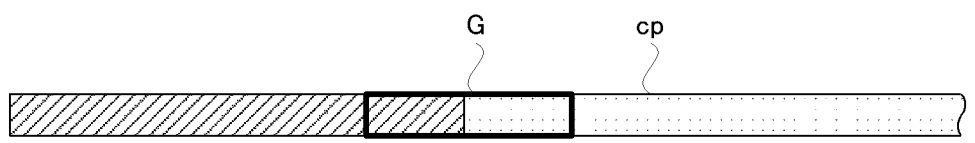

Then the boundary identifying section 12 performs filtering to the profile cp. Specifically, a differentiation filter F specified by a matrix of nine rows and one column acts on a portion of the profile cp. This is repeated for calculation of a differential value for the entire profile cp. In this way, the differentiation filter F can simply act on the entire identification region J. This is shown in FIG. 12 in detail. Firstly, the boundary identifying section 12 operates the differentiation filter F on a position G having a width by nine pixels in the first end of the profile cp (see upper part of FIG. 12.) Then the position G where the differentiation filter F acts is shifted by every one pixel of the profile cp toward the second end. Thereby a differential value of the profile cp is successively obtained (see middle part of FIG. 12.) The differential value is successively calculated in this way, and finally filtering using differentiation filter F is performed to the boundary between a dark portion where the shadow of the leaves 3b of the collimator 3a appears and a bright portion where the subject M appears (see lower part of FIG. 12.) Here, the differential value that has been continuously the value near 0 from the beginning of filtering becomes an extreme value at this portion. The differentiation filter F corresponds to the image filter in the example of the invention.

When the boundary identifying section 12 completes identification of a boundary b for the first end of the fluoroscopic X-ray image P, the differentiation filter F acts successively from the second end of the profile cp (the end opposite to the end of the profile cp shown in FIG. 12) towards the center of the profile cp, whereby a boundary b for the second end of the profile cp is identified. In this way, the boundary identifying section 12 identifies the boundary b for two points of the fluoroscopic X-ray image P.

Boundary Identifying Step S4

Figure 13:
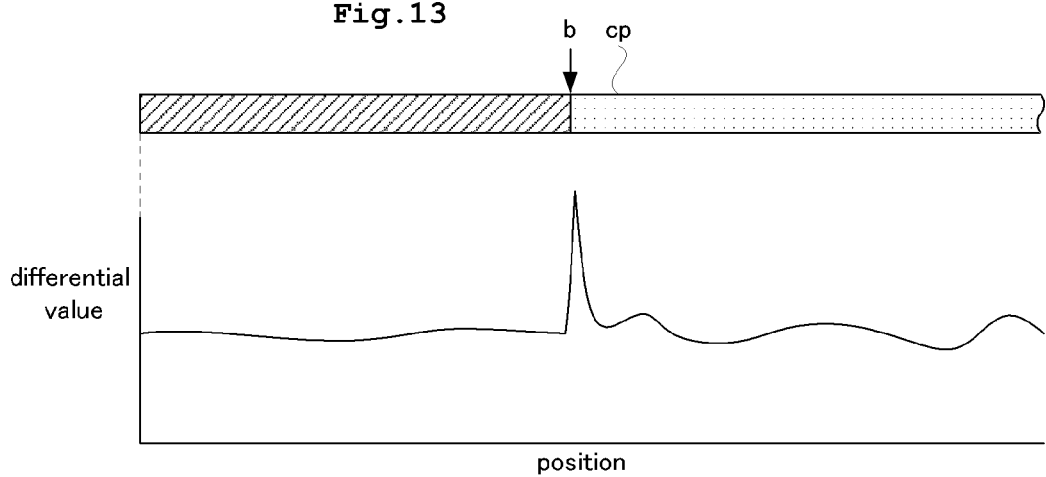

FIG. 13 shows correlation with the profile cp and the differential value. The differential value becomes extremely high between the portion derived from the shadow area R1 of the profile cp and the portion derived from the non-shadow area R2. The boundary identifying section 12 reads out a threshold memorized in the memory unit 23. Where an absolute value of the peak of the differential value exceeds the threshold, the boundary identifying section 12 identifies the peak of the differential value as the boundary b between the shadow area R1 and the non-shadow area R2, and sends position information of the boundary b to the image complement section 13. Then operations of the boundary identifying section 12 is to be completed. As noted above, the boundary identifying section 12 identifies the boundary b that appears in each of the ends in the moving direction (the upper end, the lower end) of the fluoroscopic X-ray image P.

Next, description will be given of operations of the image complement section 13. The image complement section 13 includes the fluoroscopic X-ray images P generated by the image generating section 11 and positional data on the foregoing boundary b sent thereto. The image complement section 13 complements the shadow area R1 in fluoroscopic X-ray image P with the non-shadow area R2 with reference to the boundary b, thereby generating a complement image C. Specifically, the complement image C is generated as follows.

Figure 14:
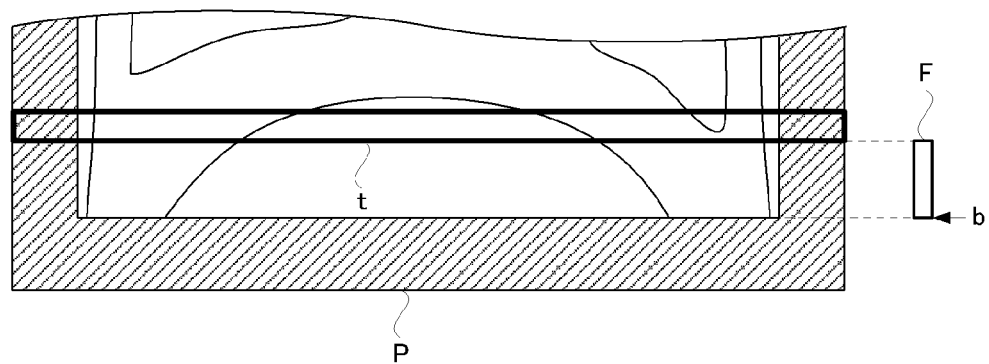
FIGS. 14 and 15 are schematic views each showing operations of an image complement section according to the example of the invention.

Firstly, the image complement section 13 sets a strip region t in the fluoroscopic X-ray image P used for complement. The setting is as under. That is, as shown in FIG. 14, the image complement section 13 firstly obtains a boundary b in the fluoroscopic X-ray image P, and obtains a position spaced away by nine pixels from the boundary b toward the non-shadow area in the longitudinal direction (i.e., a direction corresponding to the moving directions of the imaging systems 3 and 4.) Then the image complement section 13 sets the longitudinal strip region t at a position in the transverse direction (orthogonal direction.) The strip region t has a width by one pixel in the longitudinal direction, and includes both ends in the transverse direction of the fluoroscopic X-ray image P. In this way, the image complement section 13 obtains the strip region t from a position spaced away by nine pixels from the boundary b in the non-shadow area R2 of the fluoroscopic X-ray image P.

Description will be given of the meaning of setting the position spaced away by nine pixels from the boundary b as the strip region t by the image complement section 13. The width of spacing of nine corresponds to the width of the matrix in the longitudinal direction that specifies the differentiation filter F used in the foregoing filtering step S3. The differentiation filter F outputs an extreme differential value when it acts on a range across the portion derived from the shadow area R1 of the profile cp and the portion derived from the non-shadow area R2. Here, it is difficult, however, to accurately identify the position where the boundary between the shadow area R1 and the non-shadow area R2 is in the nine pixels where the differentiation filter F acts. Consequently, in order to place the strip region t accurately in the non-shadow area R2 when the boundary between the shadow area R1 and the non-shadow area R2 is located at the end of the differentiation filter F, the image complement filter 13 sets the position spaced away by nine pixels from the boundary b identified by the boundary identified section 13 toward the center of the fluoroscopic X-ray image P as the strip region t. As noted above, the image complement section 13 obtains the longitudinal strip region t belonging to the non-shadow area R2 in the fluoroscopic X-ray image P, and arranges the strip regions t longitudinally in the fluoroscopic X-ray image P, thereby generating the complement image C.

Figure 15:
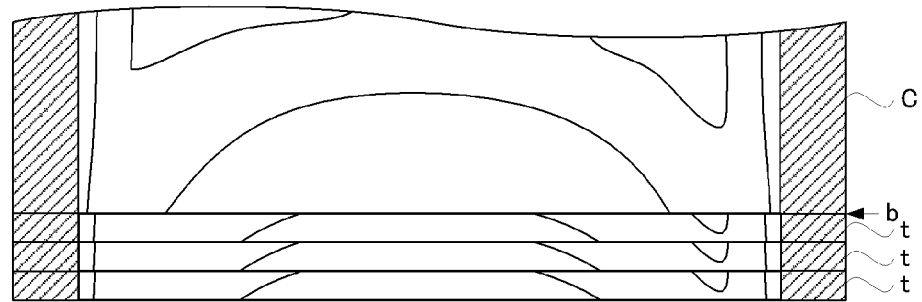
Figure 16:
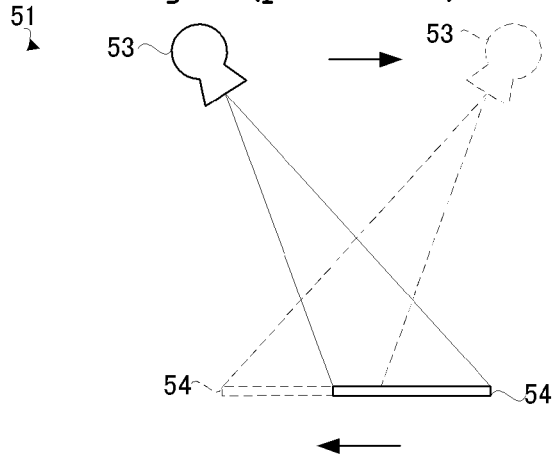
FIGS. 16 through 18 are schematic views each showing a conventional X-ray apparatus.
Figure 17:
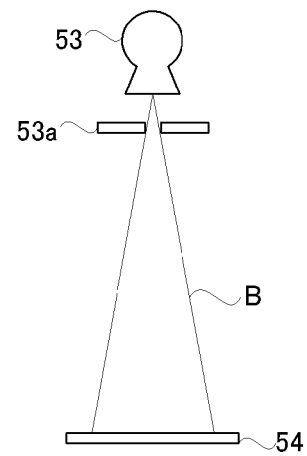
Figure 18:
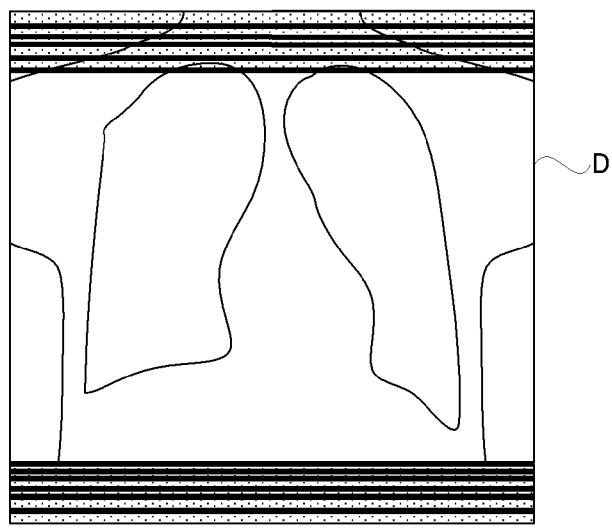

As shown in FIG. 15, the image complement section 13 arranges the strip regions t longitudinally from the boundary b toward the lower end of the fluoroscopic X-ray image P, thereby complementing the shadow area R1 in the fluoroscopic X-ray image P. Moreover, for ensuring removal of the shadow area R1 in the fluoroscopic X-ray image P, complementing may be performed from the position as a starting position that is spaced away by nine pixels from the boundary b toward the center of the fluoroscopic X-ray image P.

Operation of X-Ray Apparatus

Next, description will be given of operations of the X-ray apparatus 1. In order to take the tomographic image D with the X-ray apparatus 1 according to Example 1, the subject M is firstly placed on the top board 2. When an operator instructs obtaining of the fluoroscopic X-ray image P through a console 26, the synchronous movement controller 8 moves the X-ray tube 3 and the FPD 4 to a given initial position. The imaging systems 3 and 4 here are arranged as shown in FIG. 1 by the solid lines. That is, the X-ray 3 in the initial position is located in the front part in the body axis direction A (the longitudinal direction of the top board 2) whereas the FPD 4 in the back part in in the body axis direction A. Here, the X-ray tube 3 is inclined to an initial angle of −20 degrees.

The X-ray tube controller 6 controls the X-ray tube 3. The X-ray tube 3 irradiates the FPD 4 with an X-ray beam with a given pulse width, a tube current, and a tube voltage. The X-ray beam transmits the top board 2 into the FPD 4. The image generating section 11 constructs the detection signals outputted from the FPD 4 into the fluoroscopic X-ray image P.

The synchronous movement controller 8 moves the X-ray tube 3 and the FPD 4 synchronously and in opposite directions to each other. The X-ray tube controller 6 emits an X-ray beam intermittently during movement. The image generating section 11 generates the fluoroscopic X-ray image P at every emitting. In this way, a series of fluoroscopic X-ray images P is generated. Here, the synchronous movement controller 8 moves the X-ray tube 3 to the back part of the body axis direction A, and moves the FPD 4 to the front part of the body axis direction A.

Then the synchronous movement controller 8 moves the X-ray tube 3 and the FPD 4 into a given final position. The imaging systems 3 and 4 at this time are arranged as shown in FIG. 1 by alternate long and short dash lines. That is, the X-ray 3 in the final position is located in the back part of the body axis direction A (the longitudinal direction of the top board 2) whereas the FPD 4 in the front part of the body axis direction A. At this time, the X-ray tube 3 is inclined to the final angle of 20 degrees. The final fluoroscopic X-ray image P is obtained in this state. Then obtaining of a series of fluoroscopic X-ray images P is completed. In Example 1, 74 fluoroscopic X-ray images P are obtained.

The boundary identifying section 12 identifies the boundary b for every generation of the fluoroscopic X-ray image P.

Specifically, the boundary identifying section 12 searches the boundary b from the first end of the fluoroscopic X-ray image P, thereby identifying the boundary b. Thereafter, the boundary identifying section 12 searches the boundary b from the second end of the fluoroscopic X-ray image P, thereby identifying again the boundary b. Consequently, the shadow of the leaves 3b of the collimator 3a appearing on both ends of the fluoroscopic X-ray image P in the longitudinal direction can be identified.

The image complement section 13 complements the shadow area R1 on both ends of the fluoroscopic X-ray image P in the longitudinal direction for every identification of the boundary b. The complement image C generated in such manner is sent out to the superimposing section 14. Then a series of complement images C are sent out to the superimposing section 14. The superimposing section 14 superimposes the series of complement images C while shifting them in the body axis direction of the subject M, thereby generating a tomographic image D where a tomogram of the subject M in a given cut surface appears. The tomographic image D contains the tomogram of the subject M suitable for diagnosis and independent of influences of the shadow area R1. The tomographic image D is displayed on the display unit 27 to complete the operations As noted above, the X-ray tomography apparatus according to Example 1 is provided with a collimator 3a for collimating X-rays emitted from the X-ray tube 3. The fluoroscopic X-ray image P contains the shadow area R1 where the shadow of the collimator 3a appears. According to Example 1, the boundary between the shadow area R1 and the non-shadow area R2 in the fluoroscopic X-ray image P is identified, and the shadow area R1 in the fluoroscopic X-ray image P is complemented by the non-shadow area R2. Thereby the complement image C is generated. Then the complement image C is used for generating the tomographic image D. Since the collimator 3a is provided in order to restrict the range of X-ray irradiation, no X-ray transmits the collimator 3a. Consequently, the shadow area R1 in the fluoroscopic X-ray image P has a pixel value extremely smaller than the shadow area R2. According to Example 1, the extremely dark area is removed and thereafter the tomographic image D is generated. As a result, the tomographic image D has superior visibility with no blurring due to the shadow of the collimator 3a.

Moreover, the boundary identifying section 12 identifies the boundary extending orthogonally in the fluoroscopic image and appearing on ends of the fluoroscopic image in the moving direction. The image complement section 13 obtains a strip region t in the non-shadow area R2 of the fluoroscopic image P that laterally extends in the orthogonal direction, and arranges the strip regions t in the shadow area R1, thereby complementing the shadow area R1. Such configuration can achieve enhanced visibility at the ends of the tomographic image D in the moving direction having especially extreme blurring.

The differentiation filter F in the foregoing configuration is operated from the first end toward the center of the identification region J in the moving direction in the profile cp. Here the shadow of the collimator 3a appears at the periphery of the fluoroscopic image P. Thus, when the differentiation filter F acts on the fluoroscopic image P from the end thereof, the boundary can be identified more immediately.

Moreover, the differentiation filer F is operated to identify the boundary on the first end in the profile cp and thereafter operated from the second end in the profile cp to identify another boundary. Since the shadow of the collimator 3a generally appears in both ends of the fluoroscopic image P, such configuration can achieve immediate identification of the two boundaries.

Moreover, according to the method using the differentiation filter F, it is difficult to accurately identify the boundary between the shadow area R1 and the non-shadow area R2. According to Example 1, the strip region t is obtained from a position spaced somewhat away from the boundary in the non-shadow area R2 for ensuring location of the strip region t in the non-shadow area R2. Here, it is sufficient that the strip region t is spaced away from the boundary by a distance of the number of rows of the differentiation filter.

This invention is not limited to the foregoing example, but may be modified as follows:

(1) The foregoing example discusses a medical apparatus. This invention is applicable also to apparatus for industrial use and for the nuclear field.

(2) X-rays used in the foregoing example are an example of radiation in this invention. Therefore, this invention may be adapted also for radiation other than X-rays.

(3) In the foregoing example, the shadow area R1 is complemented by the strip region t as a portion of the non-shadow area R2. This invention, however, is not limited to this configuration. Instead of operations using the strip region t, the shadow area R1 may be complemented through replacing the pixel value of the shadow area R1 with the average value of the pixel value of the non-shadow area R2. The pixel value indicated by the average value is nearer to the pixel value of the shadow area R1 than the pixel value of the non-shadow area R2. Here, the average value is one example of the complement value in this invention.

(4) Moreover, instead of operations using the strip region t, the shadow area R1 may be complemented through replacing the pixel value of the shadow area R1 with a given replacement value (gray value) determined prior to radiography. Here, the replacement value is determined after performing X-ray tomography under the same conditions as the fluoroscopic X-ray image P, and is memorized in the memory unit 23. The pixel value indicated by the replacement value is nearer to the pixel value of the shadow area R1 than the pixel value of the non-shadow area R2. Here, the replacement value is one example of the complement value in this invention.

(5) Moreover, instead of operations using the strip region t, image processing may be performed that removes the peak of the differential value in FIG. 13. Specifically, smoothing may be performed to a region across the boundary b in the longitudinal direction of the fluoroscopic X-ray image P. That is, according to this modification, the image complement section 13 performs filtering around the shadow area R1 instead of replacing the pixel value. Thereby the pixel value in the shadow area R1 is complemented with reference to the pixel value in the non-shadow area R2.

INDUSTRIAL UTILITY

As described above, this invention is suitable for radiographic apparatus for medical uses.

The invention claimed is:
1. A radiation tomography apparatus comprising:
a radiation source for irradiating a subject with radiation;
a collimator for collimating radiation from the radiation source;
a radiation detecting device for detecting radiation applied to the subject;
a top board between the radiation source and the radiation detecting device for supporting the subject placed thereon;

a moving device for moving the radiation source and the radiation detecting device synchronously in opposite directions to each other along the top board;

a movement controlling device for controlling the moving device;

an image generating device for generating a fluoroscopic image in accordance with detection signals outputted from the radiation detecting device;

a boundary identifying device for identifying from the fluoroscopic image a boundary between a shadow area in the fluoroscopic image and a non-shadow area, in the shadow area a shadow of the collimator appearing and in the non-shadow a shadow of the collimator not appearing;

an image complement device for generating a complement image through complementing the shadow area in the fluoroscopic image with a complement value with reference to the boundary, the complement value indicating a pixel value of the non-shadow area or indicating a pixel value nearer to that of the non-shadow area than that of the shadow area; and a superimposing device for superimposing a series of the complement images generated from a series of the fluoroscopic images that are continuously taken while the radiation source and the radiation detecting device move to generate a tomographic image.

2. The radiation tomography apparatus according to claim 1, wherein the boundary identifying device identifies the boundary that extends in a direction orthogonal to a moving direction on ends of the fluoroscopic image in the moving direction, and the image complement device generates the complement image through obtaining a strip region in the non-shadow area of the fluoroscopic image that laterally extends in the orthogonal direction and arranging the strip regions in the shadow area of the fluoroscopic image in the moving direction.

3. The radiation tomography apparatus according to claim 2, wherein the boundary identifying device identifies the boundary through operating an image filter successively while moving it in the moving direction in the fluoroscopic images, the image filter acting on a partial range of an identification region that extends longitudinally along the moving direction in the fluoroscopic image.

4. The radiation tomography apparatus according to claim 3, wherein the boundary identifying device operates the image filter successively from a first end toward a center of the identification region in the moving direction.

5. The radiation tomography apparatus according to claim 4, wherein the boundary identifying device identifies the boundary on the first end in the moving direction in the identification region and thereafter identifies a boundary on a second end in the moving direction in the identification region through operating the image filter successively from the second end toward the center of the identification region, and the image complement device complements each two shadow areas in the fluoroscopic image with reference to the positions of the two identified boundaries.

6. The radiation tomography apparatus according to claim 3, wherein the image filter used by the boundary, identifying device is a differentiation filer with a matrix of m rows and n columns.

7. The radiation tomography apparatus according to claim 6, wherein the differentiation filter has the rows arranged in the moving direction in the fluoroscopic image, and the image complement device obtains the strip region from a position that is spaced away from the boundary by an m-pixel in the non-shadow area of the fluoroscopic image.

8. The radiation tomography apparatus according to claim 3, wherein the boundary identifying device averages the identification regions having an orthogonal width in an orthogonal direction and generates a profile with the orthogonal pixel width corresponding to one pixel, and the image filter acts on the profile.

* * * * *